United States Patent [19]

Ludlow et al.

[11] Patent Number: 5,043,591

[45] Date of Patent: Aug. 27, 1991

[54] PORTABLE PARTICLE ANALYSERS HAVING PLURAL DETECTORS

[75] Inventors: Ian K. Ludlow, Welwyn Garden City; Paul H. Kaye, Kimpton, both of England

[73] Assignee: The Secretary of State for Defence in Her Britannic Majesty's Goverment of the United Kingdom of Great Britain and Northern Ireland, London, United Kingdom

[21] Appl. No.: 476,397

[22] PCT Filed: Nov. 10, 1988

[86] PCT No.: PCT/GB88/00974

§ 371 Date: Jun. 4, 1990

§ 102(e) Date: Jun. 4, 1990

[87] PCT Pub. No.: WO89/04472

PCT Pub. Date: May 18, 1989

[30] Foreign Application Priority Data

Nov. 10, 1987 [GB] United Kingdom ............... 8726305

[51] Int. Cl.[5] ............................................. G01N 15/06
[52] U.S. Cl. .................................... 250/574; 250/575; 356/343
[58] Field of Search ............... 250/574, 575; 356/338, 356/336, 341, 342, 343

[56] References Cited

U.S. PATENT DOCUMENTS 4,200,802 4/1980 Salzman et al. ................... 250/461

FOREIGN PATENT DOCUMENTS 2535051 10/1982 France .
2041516A 9/1980 United Kingdom .

OTHER PUBLICATIONS

Aerosol Measurement, editor D. Lundgren, published 1979 Gainerville, (US) R. W. Storey: "Aerosol Field Measurements Using Light-Scattering Photometers", pp. 241-259, see pp. 241-244: Instruments.
International Search Report.

Primary Examiner—David C. Nelms
Assistant Examiner—Que T. Le
Attorney, Agent, or Firm—Nixon & Vanderhye

[57] ABSTRACT

A portable particle analyzer is compact and can determine the size, geometry and number of particles in a sample of fluid. A laser beam (15) intercepts the flow of fluid (17) at the first focal point of a parabolic mirror (11). Light is scattered and collected by radiation collectors (13) and low angle scattered radiation is detected in a second chamber (19) by reflection by an ellipsoid mirror (20) towards a radiation collector (21). Photomultiplier units (23) convert the radiation collected into electrical signals for analysis.

19 Claims, 3 Drawing Sheets

PORTABLE PARTICLE ANALYSERS HAVING PLURAL DETECTORS

BACKGROUND OF THE INVENTION

1. Field of the Invention

This invention relates to apparatus for the analysis of fluidborne particles. For examples, in the study of aerosols, aerosol dispersion and airborne particulate pollution control, there is a requirement for the rapid determination of particle size distribution especially in the diameter range 1 to 10 microns, together with some knowledge of the geometry and symmetry of individual particles. The latter information could, for example, enable particles with spherical symmetry to be identified and thus allow the counting/monitoring of liquid droplets in an environment including other solid, non-spherical particles. In the context of the present specification, the term particles is intended to apply both to solid bodies and to drops of liquid.

It is desirable for such apparatus to be able to count individual particles in a sample at rates of, typically 20,000 particles per second, to be able to distinguish between spherical and non-spherical particles in the sample and to count each type. Another desirable feature is to categorise spherical particles having diameters of a few microns into a number of size bands and also in this connection to classify particle coincidences as 'non-spherical' and hence to ignore them in the compilation of size spectra based on the assumption the particle is spherical.

2. Field of Prior Art

The normal techniques for the examination of particles, as used in several instruments available commercially, employ the detection and analysis of electromagnetic radiation scattered by the particles. All such instruments use a mechanical mechanism to drive the sample air through a "sensing volume" where the carried particles are illuminated by the incident electromagnetic radiation. The radiation scattered by the particles is received by one or more detectors which convert the energy to electrical signals from which information may be extracted by appropriate electrical circuits.

Particle analysers are known, for example, as described in UK Patent Application numbers 8619050, 2044951A and U.S. Pat. No. 3,946,239. These all describe analysers which comprise a concave reflector in a scatter chamber, and a flow of sample fluid intercepted by a beam of radiation. The light scattered from individual particles in the fluid is directed by the reflector to radiation collectors and subsequently analysed. All of these, however, suffer from being cumbersome and fragile and consequently not readily portable. Moreover, light scattered at low angles from the particles in the sample is not detected by any of the above prior art systems.

Another analyser is described in UK Patent number 2041516 which discloses a particle analyser of the type described above but which has an additional feature in that the concave reflector has a transparent window in it which is used to collect back scattered light by use of lenses and photomultipliers. The intensity of the back scattered light achieved by this apparatus is very low and passes through collimation means before being collected by photomultipliers. This means that not all back scattered radiation will be detected and the apparatus required to collect the light is complex, cumbersome and relatively expensive. Moreover, the apparatus is not portable.

SUMMARY OF THE INVENTION

There is therefore a need for a particle analyser which is portable compact and relatively inexpensive and determines the size, geometry and number of particles in a sample fluid, and is additionally capable of effectively and efficiently detecting and analysing light scattered at low angles from the individual particles in the sample.

According to one aspect of the present invention a particle analyser includes a first scatter chamber, means for providing a sample of fluid in the form of a laminar flow through the first scatter chamber, a beam of radiation, adapted to intercept the sample at right angles to a direction of flow of the sample at a focal point of a first concave reflector, the first concave reflector being used to direct the radiation scattered by individual particles in the sample towards at least one radiation collector, means for converting the radiation collected into electrical signals for processing and analysis, and means for dumping the non-scattered radiation characterised in that an aperture in the first concave reflector leads to a second scatter chamber comprising a second concave reflector with a radiation collector located at its near focal point and positioned so that its far focal point is at the point of interception of the beam of radiation and the sample.

The beam of radiation may be provided by a laser which may be mounted in any one of a number of ways so that the beam intercepts the sample flow at right angles. For example, it may be mounted aligned with the principal axis of the first concave reflector; such an arrangement would make the apparatus more rugged and compact.

The first concave reflector may be a parabolic mirror, or, alternatively may be an ellipsoid mirror, which would reflect the scattered light to a single point of detection.

The advantage of having a second chamber mounted coaxially with the first chamber is so that light scattered at low angles from the individual particles in the sample can be detected and analysed also. This information is particularly useful in determining the size of particles. The second chamber also includes a second concave reflector. The second concave reflector is preferably an ellipsoid minor and has a radiation collector located at a near focal point and a far focal point at the point of interception of the beam and sample. Thus, light scattered at low angles is reflected by the ellipsoid mirror to the near focal point and collected by the radiation collector there. Radiation collectors of any suitable type may be used in the present invention and may include photomultiplier units, optical fibre leading to such units or lenses directing the radiation to a photomultiplier unit or optical fibre.

According to a second aspect of the present invention a method of particle analysis includes the steps of:

passing a sample of fluid in the form of a laminar flow through a first scatter chamber;

Passing a beam of radiation through the first scatter chamber so as to intercept the sample at right angles to a direction of flow at a focal point of a first concave reflector, the first concave reflector being used to direct the radiation towards at least one radiation collector; characterised in that the back scattered radiation is collected in a second chamber, including a second concave reflector and leading from an aperture in the first concave reflector, by use of a radiation collector located at a near focal point of the second concave reflector which is also positioned so that its far focal point is at the point of interception of the beam of radiation and the sample; converting the radiation collected into electrical signals, processing and analysing the electrical signals; and dumping the non-scattered radiation.

The sample may be an aerosol.

BRIEF DESCRIPTION OF THE DRAWINGS

The number of embodiments of the invention will now be described by way of example only, with reference to the accompanying drawings, in which.

DETAILED DESCRIPTION OF EMBODIMENTS

Figure 1A:
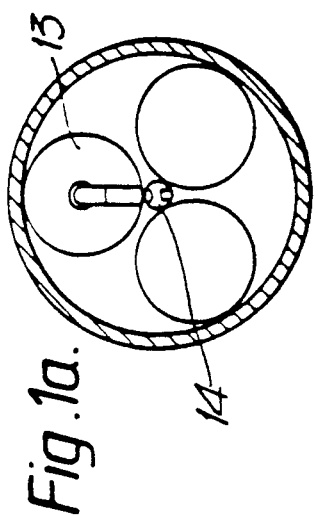
FIG. 1a is a view along the line in FIG. 1.

As shown in FIG. 1a first scattering chamber 10 includes a first concave reflector in the form of a parabolic mirror 11, lenses 12, and radiation collectors 13. A laser 14 is mounted aligned with the principal axis of the parabolic mirror 11 and directs a beam 15 of radiation towards the focal point 16 of the parabolic mirror 11 where it intercepts with the sample fluid 17 in the form of a laminar flow. An aperture 18 leads to a second chamber 19 which includes a second concave reflector in the form of an ellipsoid reflector 20 and a radiation collector 21 located at the near focal point of the ellipsoid reflector 20 and the ellipsoid reflector is positioned so that its far focal point is situated at the focal point 16 of the first parabolic reflector 11. A beam dump 22, typically a Raleigh horn is located at an aperture in the ellipsoid mirror 20 to collect the non-scattered radiation. Radiation collectors 13 and 21 are connected to photomultiplier tubes 23. FIG. 1a shows a possible arrangement of radiation collectors 13 around the laser 14. Although only three collectors are shown here, any number of detectors may be located radially around the laser 14.

Figure 1:
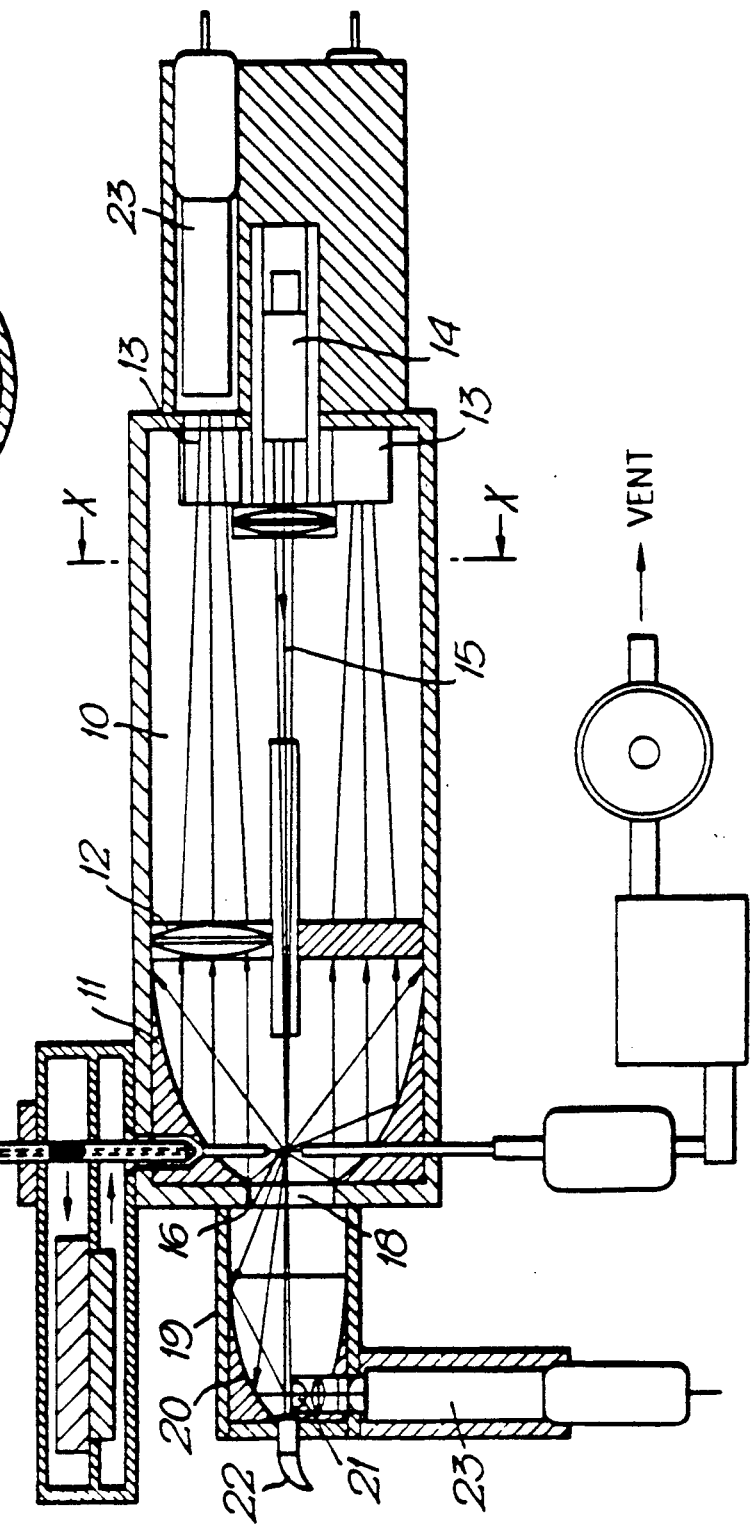
FIG. 1 is a side view in section of a preferred embodiment of the invention.
Figure 2:
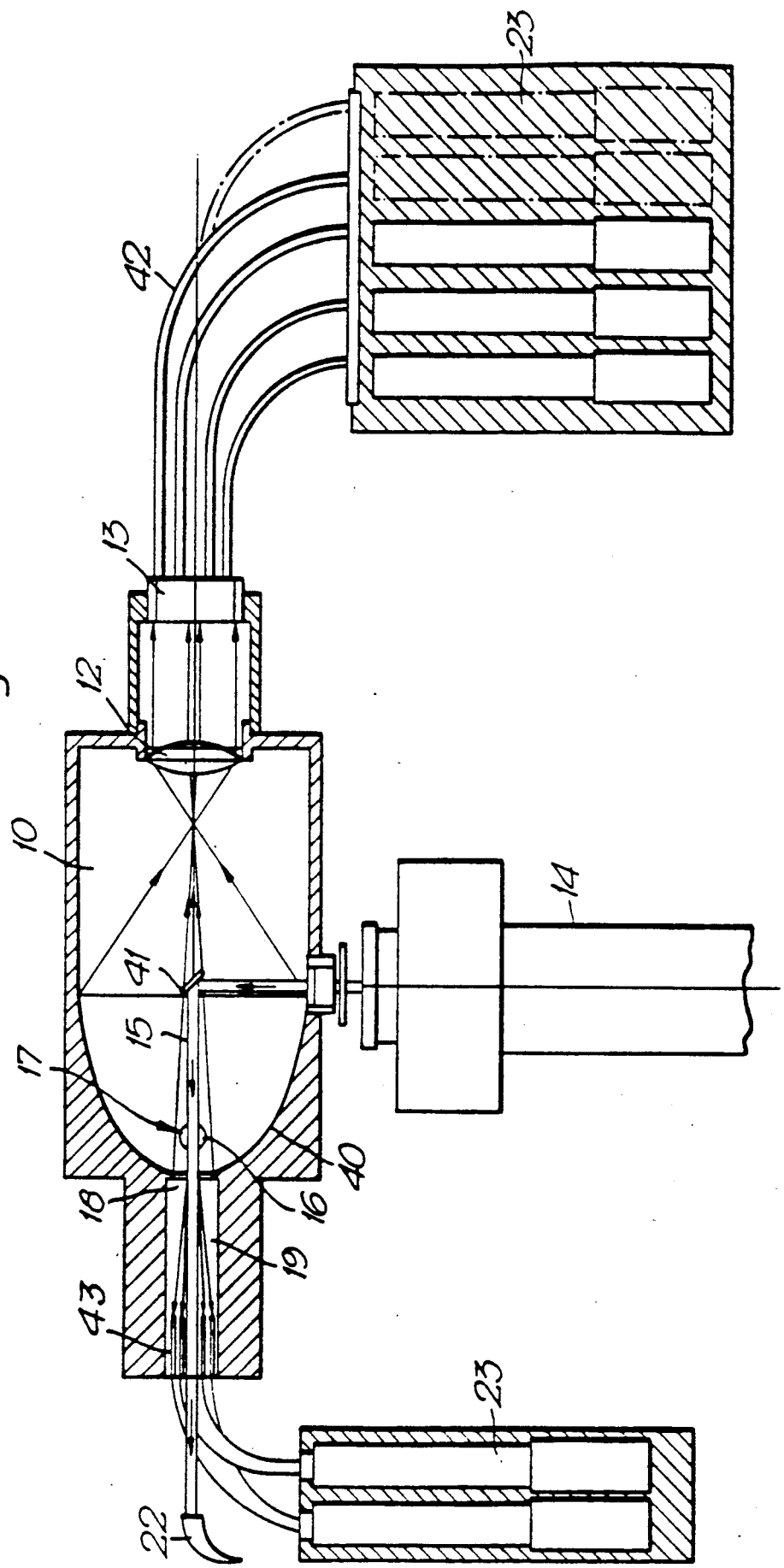
FIG. 2 is a side view in section of another embodiment of the invention.
Figure 3:
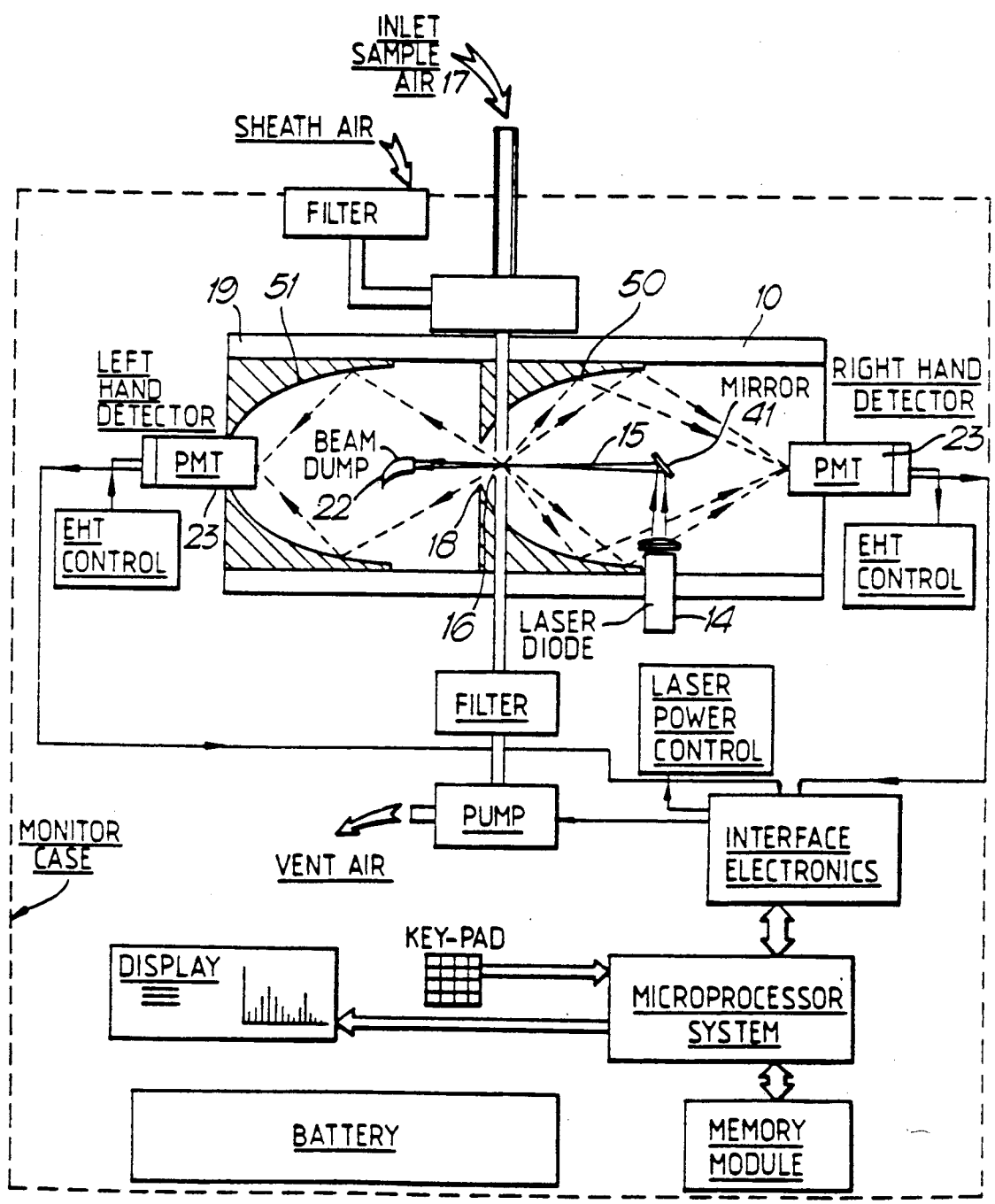

Another embodiment of the invention is shown in FIG. 2. In this embodiment both a first concave reflector 50 and a second concave reflector 51 are ellipsoid mirrors. Once again, the laser 14 is at an angle of 90° to the principal axes of the reflectors, so that mirror 41 directs the beam 15 along the principal axis. The sample 17 is directed at right angles to the laser beam 15 and intercepts it at the near focal point 16 of the first ellipsoid reflector 50. The second ellipsoid reflector 51 is positioned so that its far focal point coincides with point 16. Photomultiplier tubes 23 are located at the far focal point of the first concave reflector 50 and at the near focal point of the second concave reflector 51 to collect the scattered radiation. The beam dump 22 is located within the second scatter chamber 19 to dump the non-scattered radiation. The radiation collector 23 in FIG. 2 is positioned to face the aperture 18 in the first chamber 10 as opposed to being placed at 90° to this direction as shown in FIG. 1. The latter arrangement would collect relatively more radiation of low angle deflection, but less overall since only deflections in the direction of the face of the collector will be recorded.

In use, the sample of fluid 17 is supplied in laminar flow by means of a sheath of constant velocity air being supplied around the sample, as shown in FIGS. 1 and 2. This is so that the outer parts of the sample flow have the same velocity as the inner parts. The outer parts of the sample would otherwise flow more slowly due to friction with stationary air next to the sample flow. Additionally, a coaxial tube supplying the sheath of air is designed to dynamically focus particles in the sample to provide a laminar flow of particles. The laser beam 15 intercepts at right angles the flow of fluid 17 and light is scattered from the individual particles contained in the fluid. The scattered radiation reflects off the walls of the first concave reflector in the first scatter chamber 10. If first concave reflector is a parabolic mirror (FIG. 1) the radiation is reflected parallel to its principal axis or if it is an ellipsoid mirror 50 (in FIG. 2), the radiation is directed to the far focal point of the mirror. This deflected radiation is then directed towards photomultiplier tubes 23 either directly, as in FIG. 2, or by using lenses 12 as in FIG. 1 to direct the radiation towards the photomultiplier units 23.

Radiation scattered at low angles by the particles is collected in the second chamber 19, which may include an ellipsoid mirror 20 and 51 in FIGS. 1 and 2 and radiation collectors which may be a photomultiplier tube 23 as in FIG. 2 or a lens 21 in FIG. 1 leading to such a tube 23.

All the radiation collected is then converted into electrical signals, processed and analysed, and the information may be extracted by appropriate electronic circuits.

Although this invention has been described by way of example and with reference to possible embodiments thereof, it is to be understood that modifications or improvements may be made without departing from the scope of the invention as defined in the appended claims.

We claim:

1. A particle analyser including a first scatter chamber, means for providing a sample of fluid in the form of a laminar flow through the first scatter chamber, a beam of radiation, adapted to intercept the sample at right angles to a direction of flow at a focal point of a first concave reflector, the first concave reflector being used to direct the radiation scattered by individual particles in the sample towards at least one radiation collector, means for converting the radiation collected into electrical signals for processing and analysis, and means for dumping the non-scattered radiation characterised in that an aperture in the first concave reflector leads to a second scatter chamber comprising a second concave reflector with a radiation collector located at its near focal point and positioned so that its far focal point is at the point of interception of the beam of radiation and the sample.

2. A particle analyser as claimed in claim 1 characterised in that the beam of radiation is supplied by a laser.

3. A particle analyser as claimed in claim 2 characterised in that the laser is mounted on and aligned with the principal axis of the first concave reflector.

4. A particle analyser as claimed in claim 1 characterised in that a small reflector is mounted on the principal axis of the concave reflector to reflect the beam from a laser mounted at an angle to the principal axis.

5. A particle analyser as claimed in claim 4 characterised in that the angle is 90 degrees.

6. A particle analyser as claimed in claim 1 characterised in that the first concave reflector is a parabolic reflector.

7. A particle analyser as claimed in claim 1 characterised in that the first concave reflector is an ellipsoid with the point of interception at the proximal focal point, and a radiation collector at or near the distal focal point.

8. A particle analyser as claimed in claim 1 characterised in that the second concave reflector is a parabolic reflector.

9. A particle analyser as claimed in claim 1 characterised in that the second concave reflector is an ellipsoidal reflector.

10. A particle analyser as claimed in claim 1 characterised in that the or each radiation collector is a photomultiplier unit.

11. A particle analyser as claimed in claims 1 characterised in that the or each radiation collector is a lens directing the radiation up to a photomultiplier unit or an optical fibre.

12. A method of particle analysis including the steps of: passing a sample of fluid in the form of a laminar flow through a first scatter chamber; passing a beam of radiation through the first scatter chamber so as to intercept the sample at right angles to a direction of flow at a focal point of a first concave reflector, the first concave reflector being used to direct the radiation towards at least one radiation collector; characterised in that the back scattered radiation is collected in a second chamber, including a second concave reflector and leading from an aperture in the first concave reflector, by use of a radiation collector located at the near focal point of the second concave reflector which is positioned so that its far focal point is at the point of interception of the beam of radiation and the sample; converting the radiation collected into electrical signals; processing and analysing the electrical signals; and dumping the non-scattered radiation.

13. A method of particle analysis as claimed in claim 12 characterised in that the sample is an aerosol.

14. A particle analyser as claimed in claim 2 characterized in that the first concave reflector is a parabolic reflector.

15. A particle analyser as claimed in claim 3 characterized in that the first concave reflector is a parabolic reflector.

16. A particle analyser as claimed in claim 4 characterized in that the first concave reflector is a parabolic reflector.

17. A particle analyser as claimed in claim 5 characterized in that the first concave reflector is a parabolic reflector.

18. A particle analyzer for analyzing particles contained in a fluid, said analyzer comprising:
a first scatter chamber;
means for providing a sample of said fluid in a laminar flow through said first scatter chamber;
a first concave reflector, located in said first scatter chamber, having a focal point in said first scatter chamber and including an aperture;
a second scatter chamber connected to said first scatter chamber through said aperture;
means for providing a beam of radiation for intercepting said sample of fluid at right angles to said laminar flow at a focal point of said first concave reflector;
a first radiation collector means for collecting radiation scattered by particles in said fluid towards said first concave reflector, said first concave reflector comprising a means for directing radiation scattered by said individual particles in said sample of fluid towards said first radiation collector;
a second concave reflector, located in said second scatter chamber, having near and far focal points, said far focal point located at said point of interception of said beam of radiation and said sample of fluid;
a second radiation collector means, located at said near focal point of said second concave reflector;
means for converting collected radiation from said first and second collector means into electrical signals for processing and analysis; and
means for dumping non-scattered radiation.

19. A method of particle analysis for analyzing particles contained in a fluid, said method comprising the steps of:
providing a first scatter chamber;
passing a sample of said fluid in a laminar flow through said first scatter chamber;
locating a first concave reflector in said first scatter chamber, having a focal point in said first scatter chamber and including an aperture;
providing a second scatter chamber connected to said first scatter chamber through said aperture;
intercepting said sample of fluid with a beam of radiation at right angles to said laminar flow at a focal point of said first concave reflector;
collecting radiation scattered by particles in said fluid towards said first concave reflector;
providing a second concave reflector, located in said second scatter chamber, having near and far focal points, said far focal point located at said point of interception of said beam of radiation and said sample of fluid;
collecting radiation scattered by particles in said fluid towards said second concave reflector near focal point;
converting collected radiation into electrical signals for processing and analysis; and
dumping non-scattered radiation.

* * * * *